US00PP07835P

United States Patent [19]

Moser

[11] Patent Number: Plant 7,835

[45] Date of Patent: Mar. 24, 1992

[54] HIBISCUS PLANT NAMED FLAMINGO

[75] Inventor: Frank C. Moser, Alva, Fla.

[73] Assignee: Yoder Brothers, Inc., Barberton, Ohio

[21] Appl. No.: 578,771

[22] Filed: Sep. 7, 1990

[51] Int. Cl.[5] ..... A01H 5/00

[52] U.S. Cl. ..... Plt./54

[58] Field of Search ..... Plt./54, 67.8, 68

*Primary Examiner*—Howard J. Locker

*Attorney, Agent, or Firm*—Foley & Lardner

[57] ABSTRACT

A Hibiscus plant named Flamingo particularly characterized by its pink flower color with a dark red eye; regular single flower form; flower diameter of 100 to 120 mm; excellent pot habit with vigorous growth, good branching and very uniform performance; flower life of a single day; easy to propagate; good resistance to Bacterial Leaf Spot, and good shipping tolerance.

2 Drawing Sheets

The present invention comprises a new and distinct cultivar of Hibiscus, botanically known as *Hibiscus rosasinensis L.*, and referred to by the cultivar name Flamingo.

Flamingo, identified as 86-270001, was originated from a cross made by Frank C. Moser in a controlled breeding program in Alva, Fla., in 1985.

The female parent of Flamingo was the cultivar identified as Weismoor Sun, an unpatented Hibiscus cultivar with single flower form, bright orange-red flower color, and a red eye.

The male parent of Flamingo was the cultivar identified as Painted Lady, an unpatented Hibiscus cultivar with single flower form, pink flower color, and a red eye.

Flamingo was discovered and selected as one flowering plant within the progeny of the stated cross by Frank C. Moser in August 1986, in ground beds in Alva, Fla.

The first act of asexual reproduction of Flamingo was accomplished when vegetative cuttings were taken from the initial selection in October 1986 in ground beds in Alva, Fla., by technicians working under the supervision of Frank C. Moser.

Horticultural examination of controlled flowerings of successive plantings has shown that the unique combination of characteristics as herein disclosed for Flamingo are firmly fixed and are retained through successive generations of asexual reproduction.

Flamingo has not been observed under all possible environmental conditions. The phenotype may vary significantly with variations in environment such as temperature and light intensity.

The following observations, measurements and comparisons describe plants grown in Alva, Fla. under greenhouse conditions which approximate those generally used in Florida for commercial potted Hibiscus production.

The following traits have been repeatedly observed and are determined to be basic characteristics of Flamingo, which, in combination, distinguish this Hibiscus as a new and distinct cultivar:

1. Pink flower color with a dark red eye.
2. Regular single flower form, with flower diameter of 100 to 120 mm.
3. Excellent pot habit with vigorous growth, good branching and very uniform performance.
4. Flower life of a single day.

5. Easy to propagate.
6. Good resistance to Bacterial Leaf Spot (Pseudomonas sp.).
7. Good shipping tolerance (bud drop resistance).

The accompanying photographic drawings show typical plant habit, flower and leaf characteristics of Flamingo, with the colors being as nearly true as possible with illustrations of this type.

Sheet 1 is a color photograph of Flamingo grown as a commercially finished pot plant, with 4 cuttings in a 15 cm pot.

Sheet 2 is a black and white photograph of the foliage of Flamingo, ranging from small or immature to relatively large and mature.

Of the commercial cultivars known to the inventor, the most similar in comparison to Flamingo is the male parent Painted Lady. Flower size, flower form and flower color of Flamingo is very similar to those same characteristics of Painted Lady. Flamingo has better overall plant habit, with better branching and more uniform performance than Painted Lady. In addition, Flamingo has much better shipping tolerance (bud drop resistance) than Painted Lady, and is much more resistant to Bacterial Leaf Spot than Painted Lady, which is very susceptible. It is worth noting that bud drop in shipping budded plants has been a severe problem in many hibiscus cultivars currently being grown. Breeding for varieties not showing this trait is a high priority breeding objective. Therefore, the trait of bud drop resistance in Flamingo is very important. Resistance to Pseudomonas sp. (Bacterial Leaf Spot) is also a very important trait. Cultivars which are very susceptible to this disease cannot be grown successfully in the Florida environment.

In the following description color references are made to The Royal Horicultural Society Colour Chart. The color values were determined on May 22, 1990 in Salinas, Calif. on plant material grown in Alva, Fla. and shipped as a budded plant to Salinas, Calif., where it was flowered.

Classification:

*Botanical.*—*Hibiscus rosasinensis L.* cv Flamingo.

*Commercial.*—Greenhouse pot Hibiscus.

INFLORESCENCE

A. Flower (general):

*Size.*—100 to 120 mm.

*Born.*—In axils of leaves, 1 per node.
*Form.*—Regular single.
*Life.*—1 day.
*Blooming habit.*—Continuously, year round.

B. Corolla (petals):
*Color (general tonality from a distance of three meters).*—Pink with red eye.
*Color (upper surface).*—52C. Eye: Very dark red, closest to 52A. Veins: Closest to 49B.
*Color (under surface).*—Left $\frac{2}{3}$ of underside petal: 52C. Right $\frac{1}{3}$: Closest to 27A, with some streaks of 52C at the base.

C. Reproductive Organs:
*Androecium (stamens)*:—Numerous anthers, abundant pollen, color 17A.
*Gynoecium (pistil).*—Stigma: 5 in number, rounded, hairy. Color: 41A. Style: 27B. Base is overlaid with 46A, dispersing to 27B toward middle of staminal column.

PLANT

A. General Appearance:
*Height.*—20 to 25 cm when grown as pot Hibiscus with 4 cuttings in a 15 cm pot and 1 to 2 applications of 400 ppm CCC.
*Branching pattern.*—Semi-upright.

B. Foliage:
*Color (upper surface).*—147A.
*Color (under surface).*—147B.
*Shape.*—See photograph.

I claim:

1. A new and distinct Hibiscus plant named Flamingo, as described and illustrated.

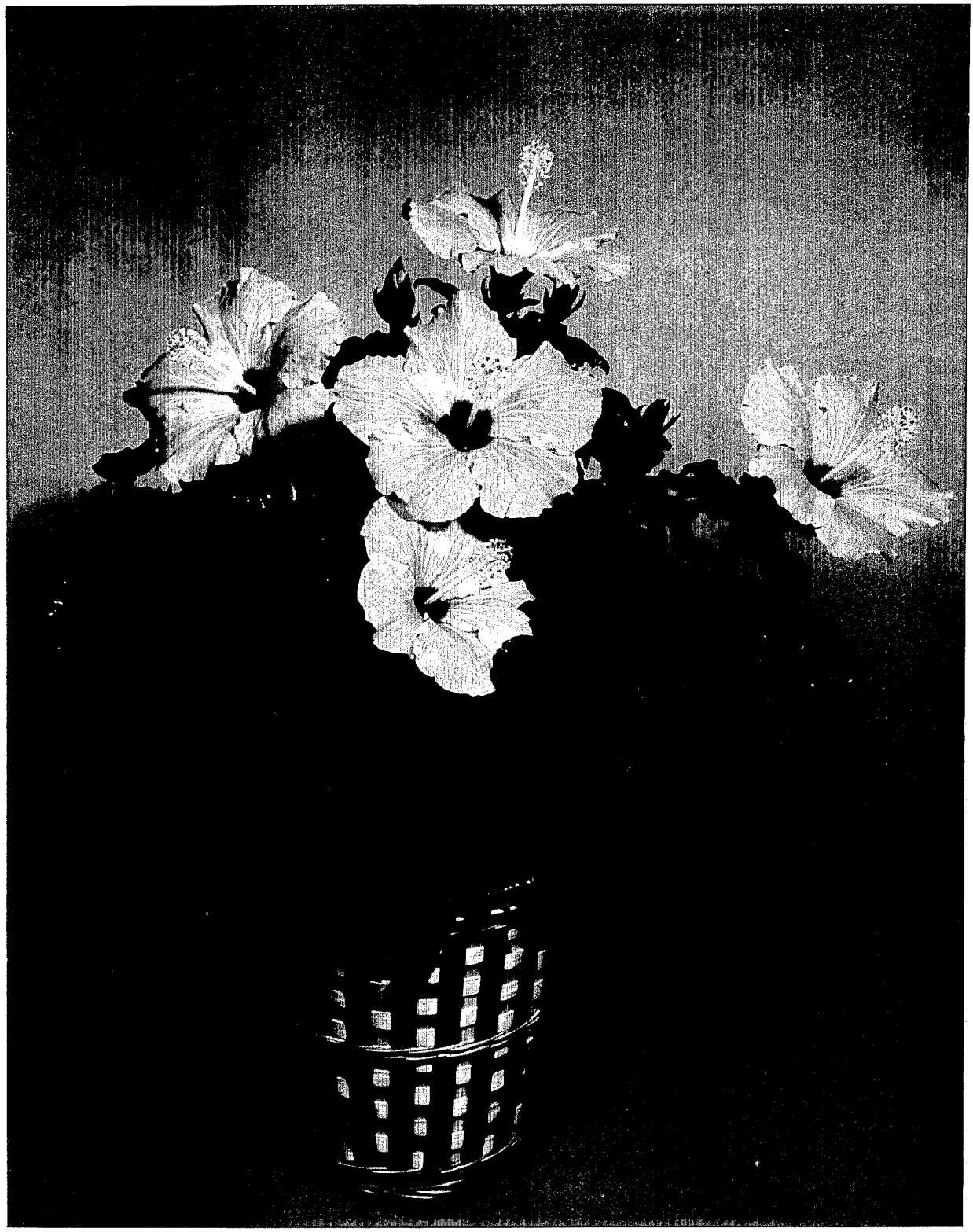

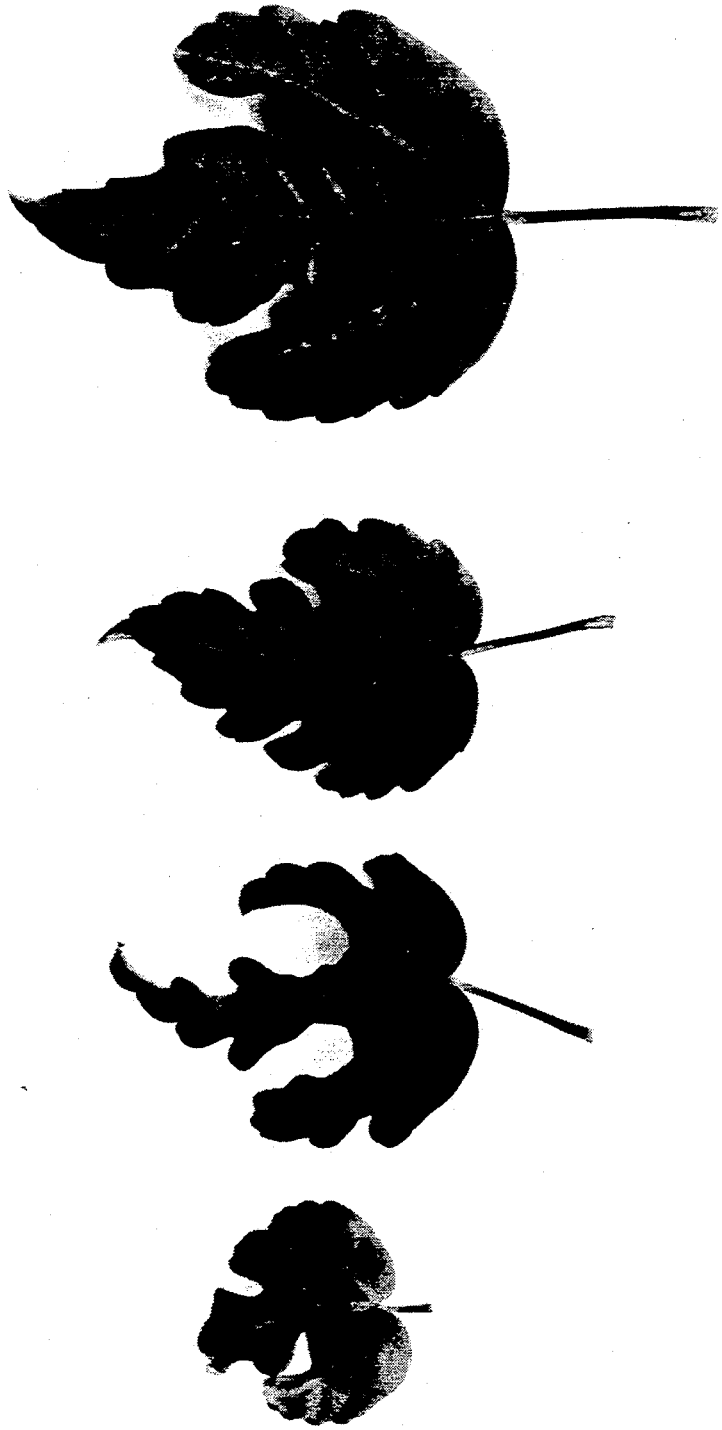

* * * * *